United States Patent
Burger et al.

[11] Patent Number: 6,034,152
[45] Date of Patent: Mar. 7, 2000

[54] PLAQUE-INHIBITING COMPOSITES

[75] Inventors: Bernd Burger, Alling; Bernd Gangnus; Rainer Guggenberger, both of Herrsching, all of Germany

[73] Assignees: THERA Patent GmbH & Co. KG; Gesellschaft fur industrielle Schutzrechte, both of Seefeld, Germany

[21] Appl. No.: 09/049,079

[22] Filed: Mar. 27, 1998

[30] Foreign Application Priority Data

Mar. 27, 1997 [DE] Germany .................. 197 13 048

[51] Int. Cl.[7] .................................................. A61K 6/00
[52] U.S. Cl. .................. 523/116; 433/228.1; 523/114; 523/118
[58] Field of Search .................. 523/116, 118, 523/114; 424/484; 433/228.1

[56] References Cited

U.S. PATENT DOCUMENTS

| | | | |
|---|---|---|---|
| 4,772,325 | 9/1988 | Kwan et al. | 106/35 |
| 4,872,936 | 10/1989 | Engelbrecht . | |
| 5,520,725 | 5/1996 | Kato et al. . | |
| 5,520,922 | 5/1996 | Gasser et al. . | |
| 5,593,303 | 1/1997 | Cohen et al. | 433/9 |
| 5,697,787 | 12/1997 | Schumacher | 433/226 |
| 5,710,194 | 1/1998 | Hammesfahr et al. | 523/116 |
| 5,824,720 | 10/1998 | Nowak et al. | 523/116 |
| 5,859,089 | 1/1999 | Qian | 523/116 |
| 5,861,445 | 1/1999 | Xu et al. | 523/116 |
| 5,873,724 | 2/1999 | Carucci | 433/215 |
| 5,876,208 | 3/1999 | Mitra et al. | 433/217.1 |
| 5,932,627 | 8/1999 | Blackwell | 523/118 |

FOREIGN PATENT DOCUMENTS 2297692  8/1996  United Kingdom .

OTHER PUBLICATIONS

Meyer et al. Compomers: Between Glass–Ionomer Cements and Composites. Biomaterials. vol. 19, No. 6, pp. 529–539. (Mar. 1998).

*Primary Examiner*—Robert H. Harrison
*Attorney, Agent, or Firm*—Birch, Stewart, Kolasch & Birch, LLP

[57] ABSTRACT

Dental composites are provided on the basis of customary polymerizable monomers, initiators, fillers and other auxiliaries, which additionally contain the plaque-inhibiting addition of salts of acid-functional polymers having mono- or polyvalent cations.

17 Claims, 1 Drawing Sheet

PLAQUE-INHIBITING COMPOSITES

FIELD OF THE INVENTION

The invention relates to the reduction of plaque accumulation on dental materials made from plastics.

Dental composite materials are used for a broad indication spectrum in dental medicine because of their good aesthetic and mechanical properties. Especially in the case of use in the field of the facing of crowns, bridges and metal frameworks for larger removable and implant-borne prostheses, it is of decisive aesthetic and hygienic importance to keep the plaque accumulation occurring in the oral environment as small as possible. Compared with dental materials on the basis of polymethyl methacry late (PMMA) or ceramics, such as for example ready-made teeth, dental composite materials tend towards an increased plaque accumulation. Against this, a plaque-inhibiting effect is described for dental amalgam and dental cements in the publications K. Larson, P. O. Glantz, Acta Odontol. Scand. 30 (1981), p. 79 and S. Minagi et al., Infect. Immun. 48 (1985), p. 11.

It is furthermore known that bacteria colonies are for the most part established, not directly on the substrate, but rather on a pellicle layer which is built up from saliva proteins within a short time in the human mouth. On hydrophilic surfaces, for example on natural teeth or ceramics, the protein adsorption is reversible, but the protein adsorption on unpolar surfaces is irreversible, as a result of which the adhesion of micro-organisms, and thus ultimately also the development of a bacterial plaque, is encouraged. Modern dental composites are characterized by relatively hydrophobic monomers, such as for example 2,2-bis-[p-2-hydroxy-3-methacryloyloxypropoxy)phenyl]-propene (bis-GMA) and 2,2,4-(2,4,4)-trimethylhexamethylene-bis-(urethanethylmethyl-methacrylate) (UDMA), in order to keep the water absorption, and thus a possible swelling and the colorability by exogenous colouring substances, small. On the other hand, this does encourage the tendency towards accumulation of plaque. Aged and mineralized plaque can no longer be removed by normal brushing of the teeth and is in most cases turned a yellowish to brownish colour by food constituents or tobacco consumption or other exogenic influences, as a result of which the affected surfaces no longer satisfy the aesthetic demands made of them.

Methods of inhibiting plaque on teeth or dental restorations are well known from the state of the art. These methods can be divided into three categories:

1. Coating of the teeth or dental restorations with films
2. Coating of the teeth or dental restorations with antibacterial films
3. Additions of antibacterial agents to the restoration materials.

Category 1

Silicone oils were suggested as an additive to toothpastes because of their hydrophobic nature. Their effect is based on the construction of a boundary layer between two hydrophilic layers, tooth and pellicle. However, the adhesion and retention at the tooth surfaces is typically low.

U.S. Pat. No. 5,078,988 (Lin et al.) discloses toothpastes with modified aminoalkyl silicones, which are to produce a hydrophobic layer on the teeth in order to-reduce-bacterial accumulations.

Plaque inhibition for plastic-based dentures is also described in EP-A-0 575 535 (Essential Dental Systems Inc., Dec. 29, 1993). After the application of a composition, consisting of solvent, volatile compound, polyurethane resin and polyfluorine compound, to the denture, the coating is fixed by air or heat drying.

PCT application WO-A-95/15740 (3M, Dec. 2, 1994) describes a coating material, transversely crosslinkable with the surface and made from copolymer units, for the reduction of plaque accumulation in dental materials. In principle, the surface is hydrophilized and a reversible adhesion of the bacterial cultures is thus made possible.

E. Budtz-Joergensen and S. Kaaber, Scandinavian Journal of Dental Research, 94 (1986), pp. 568–574, proposed coating the denture with transversely crosslinked acrylic polymers. The coating is carried out photochemically and is therefore uncomfortable and can be applied only once.

Harvey et al. (U.S. Pat. No. 5,192,362 of Sep. 3, 1993) follow the approach of applying an anionic layer, in this case made from polysaccharides, and thus reducing the adhesion of the plaque.

Category 2

WO-A-91/13608 (Rolla et al) describes toothpastes which contain a liquid silicone oil and a fat-soluble antibacterial agent, the effect being developed by the slow release of this antibacterial agent into the saliva.

Antibacterial films for increasing the storage stability of foodstuffs are known from JP-A-01186804-A (Dainippon Printing KK, 26.7.1989). These films consist of solid zeolite particles which contain metal ions having an antibacterial action, and a surface-treatment product, both dispersed in plastic.

Preparations to be used dentally which have amidobetaines or sulfobetaines as active constituents are known from DE-A-2 646 199 (Noxell Corp., Apr. 28, 1977) and have a plaque-preventing effect.

The inventors disclose in EP-A-0 404 558 (Perio Prod. Ltd., Yissum Res. & Dev. Co., Petr Prod Ltd., Dec. 27, 1990) a liquid composition which contains acrylic polymers, a pharmaceutical product and a control means for the release of the pharmaceutical product into the oral cavity, preferably a transverse crosslinker, polysaccharide, lipid, protein or amino acid, and serves to prevent plaque accumulations or treat infections in the oral cavity.

Category 3

EP-A-0 537 774 describes dental composite materials which contain antibacterial polymerizable monomers based on quaternary nitrogen compounds.

Jusan P. Loyola-Rodriguez et al., Pediatric Dentistry 16 (1994), pp. 345 et seq. describe a plaque-inhibiting influence of glass conomer cements, the antibacterial effect of which is attributed to a fluoride release of at least 140+25 ppm and the low pH value prior to the setting of the cement.

The state of the art thus describes antibacterial and anionic coatings or the use of fluoride-releasing additives as means of inhibiting plaque in dentures. In addition to the considerable time required when coatings have to be applied subsequently, and the resultant costs for all concerned, a threat to the health of dental technicians, dentists and patients can result from coatings which contain antibacterial a ctive ingredients, because of the possibility of resistance development in the case of pathogenic oral germs. There is thus a considerable demand for plastics materials which are plaque-reducing per se.

SUMMARY OF THE INVENTION

An object of the present invention is to provide a dental composite material which reduces plaque accumulation for use as a dental restoration material, in particular as a material for prostheses, temporary fixtures, facings and fillings and as a plastic for orthodontic apparatus, false teeth, stump construction, sealing or for cements.

This object is achieved by a dental composite composition on the basis of customary polymerizable monomers, initiators, fillers and other auxiliaries, which additionally contains salts of acid-functional polymers with mono- or polyvalent cations, preferably cured glass ionomer cements.

It was surprisingly found that the addition of salts of acidfunctional polymers with mono- or polyvalent cations, in particular of cured glass ionomer cements, to dental composite material produces a strong plaque-inhibiting effect, although unlike the methods known from the state of the art a scarcely detectable quantity of fluoride ions, namely less than 5 ppm, is released.

It is also surprising that not only do the composite materials according to the invention accumulate less plaque, but deposits that have nevertheless formed can be removed particularly easily, for example by conventional cleaning with toothbrushes customary in the trade.

BRIEF DESCRIPTION OF THE DRAWINGS

The illustration of FIG. 1 shows the total prosthesis of a patient in which one tooth (number 1) was treated with composite material according to the invention and one tooth (number 2) with composite material customary in the trade, after being worn for six weeks.

DETAILED DESCRIPTION OF THE INVENTION

Figure 1:
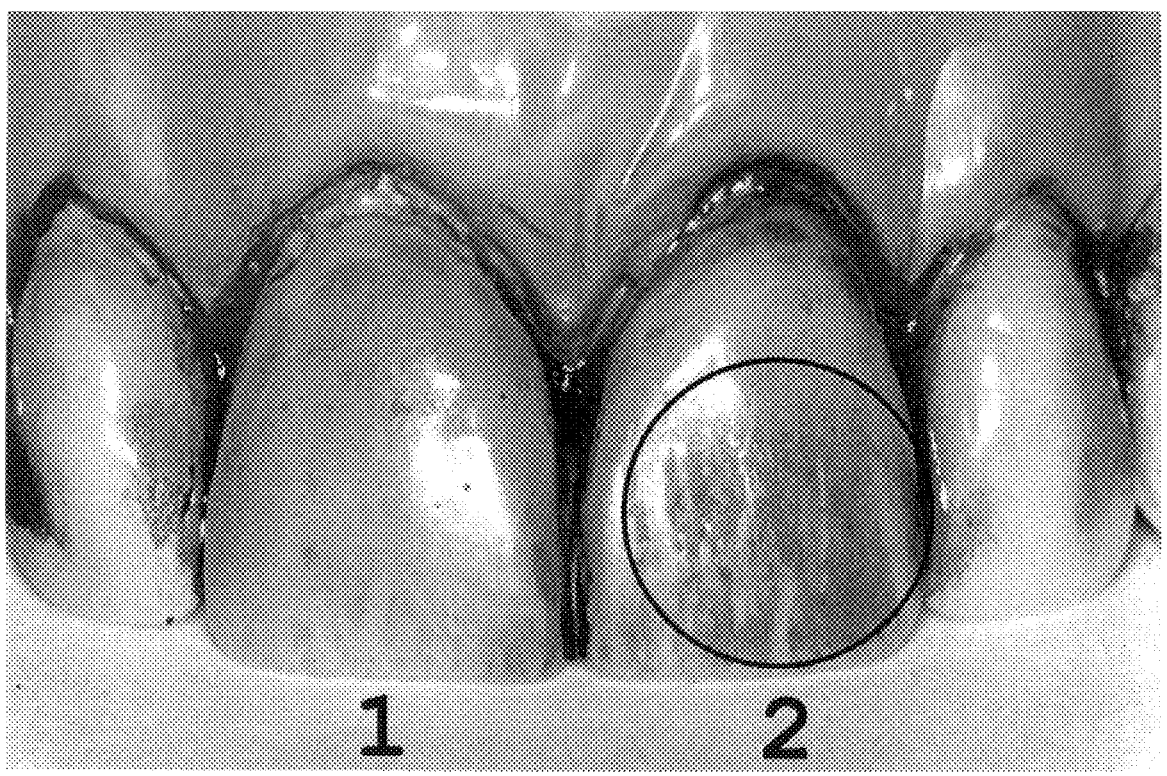

The invention relates to dental composite compositions, comprising (a) one or more ethylenically unsaturated, polymerizable monomers on the basis of mono-, di- or polyfunctional (meth)acrylates, (b) customary initiators and optionally customary activators, (c) customary fillers, (d) optionally pigments, X-ray-opaque additives, thixotrophy auxiliaries, plasticizers and other customary auxiliaries, which are characterized in that they additionally contain (e) one or more salts of acid-functional polymers having mono- or polyvalent cations, optionally in combination with inorganic glasses, i.e. in the form of cured glass ionomer cements.

The composite compositions according to the invention preferably contain the components (a) to (e) in the following quantities:

(a) 4 to 68.99 wt.-%, more preferably 45 to 55 wt.-%, (b) 0.01 to 3 wt.-%, more preferably 0.1 to 2 wt.-%, (c) 5 to 95 wt.-%, more preferably 20 to 80 wt.-%, most preferably 35 to 70 wt.-%, in particular 45 to 55 wt.-%, (d) 0 to 20 wt.-%, more preferably 0 to 10 wt.-%, and (e) 1 to 20 wt.-%, more preferably 2 to 15 wt.-%, most preferably 3 to.9 wt.-%.

All percentages are in each case related to the total weight of the composite composition including all of the present components (a) to (e).

Ethylenically unsaturated monomers or polymers, e.g. monomeric or polymeric acrylates and methacrylates, come into consideration as component (a). Reference may be in this regard to the compositions described in DE-A-3 609 038, and the X-ray-opaque fillers described there can also be included. For example, the monomeric and polymeric acrylates and in particular methacrylates may be emphasized as ethylenically unsaturated monomers or polymers. In the case of polymerizable dental compositions, the long-chained monomers of U.S. Pat. No. 3,066,112 on the basis of bisphenol -A and glycidyl methacrylate, or their derivatives obtained by adding isocyanates, are often used in particular. The acrylic acid or methacrylic acid esters of mono or preferably polyhydric alcohols, for example triethylene glycol dimethacrylate and the like, are also particularly suitable. The diacrylic and dimethacrylic acid esters of bishydroxymethyltricyclo-[$5.2.1.0^{2.6}$]-decane named in DE-A-2 816 823 are also particularly suitable. The reaction products from diisocyanates and hydroxyalkyl(meth) acrylates, as described for example in DE-A-2 312 559, can also be used. Mixtures of monomers or unsaturated polymers made therefrom can of course also be used.

All substances which trigger the polymerization after irradiation by UV or visible light, for example benzoin alkyl ether, benzil cetals, acylphosphine oxides or aliphatic and aromatic 1,2-diketone compounds, e.g. camphor quinone, can be used as photo-initiators of component (b), the light polymerization being able to be accelerated by adding activators, such as tertiary amines or organic phosphites, in a manner known per se.

U.S. Pat. No. 3,541,068 and DE-A-2 658 530 disclose anilines and xylidines suitable for this. Suitable initiator systems for triggering the polyme rization via a redox mechanism are for example the peroxide/amine or peroxide/barbituric acid derivatives systems and the like. When using such initiator systems it is advisable to keep ready an initiator (e.g. peroxide) and a catalyst component (e.g. amine) separately. The two components are then homogeneously mixed with each other shortly before use. Suitable initiator systems for triggering the polymerization via a thermal mechanism are peroxides, for example dibenzoyl peroxide or dilauroyl peroxide.

The fillers of component (c) preferably have an average grain distribution of <20 μm, in particular <5 μm and quite partiularly preferably <1.5 μm, as well as an upper grain size of 70 μm, preferably 25 μm and in particular <5 μm. Inorganic fillers can be for example quartz, ground glasses, silica gels as well as pyrogenic silicic acids or their granules. X-ray-opaque fillers can also be used, at least partially. These can be X-ray-opaque glasses, i.e. glasses which contain e.g. strontium, barium or lanthanum. For better incorporation in the polymer matrix, it is of advantage to hydrophobize the inorganic fillers. Customary hydrophobization agents are silanes, for example trimethoxymethacryloyloxypropyl silane. The quantity of silane used is customarily 0.5 to 10 wt.-%, relative to inorganic fillers, preferably 1 to 6 wt.-%, quite particularly preferably 2 to 5 wt.-%. Already finished pigmented polymethacrylate beads or other powdered inorganic polymerizates are also suitable as fillers.

Component (d) can be an X-ray-opaque addition, such as for example yttrium fluoride, strontium hexafluorozirconate or fluorides of the rare earth metals. To increase the flexibility of the compositions, it may also be advantageous to use soluble organic polymers. Suitable are e.g. polyvinyl acetate as well as the copolymers on the basis of vinyl chloride/vinyl acetate and the like. Dibutyl, dioctyl and dinonyl phthalates for example are well suited as additional plasticizers.

According to the invention, the component (e) is added to the constituents (a) to (d) for plaque inhibition in the form of one or more salts of acid-functional polymers having polyvalent cations, in particular cured glass ionomer cements. These are preferably ground to grain sizes below um. The resultant powders are mixed with composite formulations and these are processed as usual. The salts used can also be produced in other ways, for example by spray drying.

The cation portion of the salts of acid-functional polymers having polyvalent cations can be taken from the group: 1st, 2nd and 3rd main groups, 2nd and 3rd secondary groups and the lanthanides in the form of the corresponding ions. Preferred cations of the 1st main group are Li, Na and K, preferably Na. Preferred cations of the 2nd main group are Ca, Mg, Sr, Ba, calcium coming into consideration in particular. Al, Ga and In come into consideration as cations of the 3rd main group, in particular Al and In, with aluminum being particularly preferred.

From the 2nd secondary group, Zn in particular is suitable as a cation, and Sc, Y and La can be used from the 3rd secondary group, in particular Y and La. Of the lanthanides, Ce and Yb are preferred.

Suitable as the polymeric polyacid to be used are polycarboxylic acids, e.g. polymaleic acid, polyacrylic acid, polyitaconic acid and also mixtures thereof or copolymers, in particular the maleic acid/acrylic acid copolymers and/or acrylic acid/itaconic acid copolymers known from EP-A-0 024 056. The average molecular weight of the polycarboxylic acid to be used is more than 500. An average molecular weight of 1,000 to 20,000 is advantageous, and those from 3,000 to 10,000 are particularly preferred. Polyphosphonic acids, e.g. polyvinylphosphonic acid, are also suitable as the polymeric polyacid. These polyphosphonic acids can wholly or partly replace the polycarboxylic acids named above. Compounds of the cations which are not soluble in water (e.g. ZnO) are suspended in the acid solution, the precipitating salts are optionally heated in order to complete the reaction. Treatment and drying by known methods follow.

Glass ionomer cements generally-consist of:

(a) an aluminum fluorosilicate glass or an aluminum silicate glass (b) at least one polymeric polyacid having an average molecular weight of >500

(c) water (d) optionally a chelate-forming agent.

The calcium aluminum fluorosilicate glasses described in DE-A-2 061 513 and in EP-A-0 023 013 can be used as constituent (a).

Aluminum silicate glasses or aluminum fluorosilicate glasses can for example consist, apart from oxygen, of:

| Constituent | Calculated as | Wt.-% |
| --- | --- | --- |
| Si | $SiO_2$ | 2–60 |
| Al | $Al_2O_3$ | 10–50 |
| Ca | CaO | 0–40 |
| Sr | SrO | 0–40 |
| F | F | 0–40 |
| Na | $Na_2O$ | 0–10 |
| P | $P_2O_5$ | 0–10 | whereby at least 1 wt.-% CaO and/or Sro must be included and overall 0 to 20 wt.-%, calculated as oxides, B, Bi, Zn, Mg, Sn, Ti, Zr, La or other trivalent lanthanoids, K, W, Ge and also other additives which do not impair the properties and are physiologically acceptable. The glasses can be made X-ray visible by adding 10 to 20 wt.-% $La_2O_3$.

The fluoride-containing powder particles advantageously consist of:

| Constituent | Calculated as | Wt.-% |
| --- | --- | --- |
| Si | $SiO_2$ | 25–50 |
| Al | $Al_2O_3$ | 10–40 |
| Ca | CaO | 0–35 |
| Sr | SrO | 0–35 |
| F | F | 10–30 |
| Na | $Na_2O$ | 0–8 |
| P | $P_2O_5$ | 1–10 | whereby at least 10 wt.-% Ca (calculated as CaO) and/or Sr (calculated as SrO) must be included and 0 to 10 wt.-% $B_2O_2$, $Bi_2O_3$, ZnO, MgO, $SnO_2$, $TiO_2$, $ZrO_2$, $La_2O_3$, or other oxides of trivalent lanthanoids, $K_2O$, $WO_3$, $GeO_2$ and other additives which do not impair the properties and are physiologically acceptable.

Particularly preferred fluoride-containing powders used contain:

| Constituent | Calculated as | Wt.-% |
| --- | --- | --- |
| Si | $SiO_2$ | 25–45 |
| Al | $Al_2O_3$ | 20–40 |
| Ca | CaO | 10–30 |
| F | F | 10–30 |
| Na | $Na_2O$ | 1–8 |
| P | $P_2O_5$ | 1–10 |

The glass powders to be used as a constituent of a conventional glass ionomer cement have an average grain size (weight average) of at least 1 μm and preferably at least 3 μm. The average grain size (weight average) is 1 to 20 μm, preferably 3 to 15 μm and particularly preferably 3 to 10 μm. The particles have a maximum grain size of 100 μm, preferably 60 μm, in particular 20 μm.

The thus-obtained powders are then optionally subjected to a surface treatment in accordance with EP-A-0 023 013. To this end, the glass powders are superficially treated with acid, preferably at room temperature. Substahces containing acid groups are used, e.g. hydrochloric acid, sulphuric acid, nitric acid, acetic acid, propionic acid or perchloric acid, which form soluble calcium salts or strontium salts. The acids are used in a concentration of 0.01 to 10 wt.-%, preferably 0.05 to 3 wt.-%. After the corresponding reaction time, the powders are separated from the solution and thoroughly washed out, so that there are practically no longer any soluble calcium or strontium salts on the surface of the powder particles.

Powders not containing fluoride can be obtained by an additional portion, corresponding to the former fluoride portion, of 10 to 30 wt.-% oxide mixture.

The polymeric polyacids to be used as constituent (b) can be polycarboxylic acids, e.g. polymaleic acid, polyacrylic acid, polyitaconic acid and also mixtures thereof or copolymers, in particular the maleic acid/acrylic acid copolymers and/or acrylic acid/itaconic acid copolymers known from EP-A-0 024 056. The average molecular weight of the polycarboxylic acid to be used is more than 500. An average molecular weight of 1,000 to 20,000 is advantageous, and 3,000 to 10,000 are particularly preferred. The polyacid is preferably used in concentrations of 5 to 50 wt.-% relative to constituent (a). Polyphosphonic acids, e.g. polyvinyl phosphonic acid, are also suitable as polymeric polyacid. These polyphosphonic acids can wholly or partly replace the polycarboxylic acids named above.

Constituent (c), the water, is used in quantities of 5 to 70 wt.-%, preferably 15 to 40 wt.-%, relative to the total weight.

A chelate-forming agent, as is described in DE-A-2 319 715, can be included as constituent (d). Tartaric acid is preferably used as a chelate former. The chelate formers can be used in concentrations of 0.1 to 10, preferably 3 to 8 wt.-%, relative to the total mass.

In order to achieve high storage stability prior to use, an addition of preservatives is recommended, e.g. benzoic acid, in particular to the dry polyacid.

Additions to adjust the viscosity (e.g. pyrogenic silicic acid) are possible. Suitable concentrations are 0.1 to 10, preferably 1 to 5 wt.-%, relative to the total mass.

The composite compositions according to the invention are suitable in particular as materials for prostheses, temporary fixtures, facings and fillings and also as plastics for orthodontic apparatus, false teeth, stump construction, for sealing or as cements.

EXAMPLES

The invention is further explained by the following test examples, the contents of the test descriptions serving as examples only and the invention in no way being restricted to these examples.

EXAMPLE 1

The invention is particularly easily understood when the test examples described below are divided into three groups. Test group A comprising tests 1 to 7 serves for the preparation of very finely ground powder from set glass ionomer cements (1 to 5), or very finely ground powder from salts of acid-functional polymers having polyvalent cations (6 to 7). Test group B. consisting of test 8, describes a composite formulation such as is known from the state of the art. Test group C, consisting of tests 9 to 17, concerns configurations of the invention, in each of which the dental composite material from test group B is mixed with the powders from test group A and cured. Plaque accumulations are then studied in vitro and in viva, and also fluoride release in an aqueous medium, by the methods described in the following. The zeta potential at the surface of the cured composite materials becomes more negative through the addition of the polysalts according to the invention; in the case of comparable formulations this effect correlates with the extent of the plaque reduction.

The glass powder components used in each case serve as a source for polyvalent cations, the used liquids contain acid-functional polymer.

Test group A

Glass powder and liquids customary in the trade are used in the tests described below:

Glass powder 1: Ketac Fil glass powder (Espe)

Glass powder 2: Fuji II glass powder (GC)

Glass powder 3: Chemfil Superior glass powder+polymer acid (Dentsply)

Liquid 1: Ketac Fil liquid (Espe) (polymer acid+water)

Liquid 2: Durelon liquid (Espe) (polymer acid+water)

Liquid 3: Fuji II liquid (GC) (polymer acid+water)

Test 1

Glass powder 1 is mixed with liquid 1 in the ratio 2:1. The set cement is then ground to a grain size of <20 μm.

Test 2

Glass powder 1 is mixed with liquid 2 in the ratio 2:1. The set cement is then ground to a grain size of <20 μm.

Test 3

Glass powder 1 is mixed with 20% polyvinyl phosphonic acid (PVP) in the ratio 2:1. The set cement is then ground to a grain size of <20 μm.

Test 4

Glass powder 2 is mixed with liquid 3 in the ratio 2:1. The set cement is then ground to a grain size of <20 μm.

Test 5

Glass powder 3 is mixed with distilled water in the ratio 7:1. The set cement is then ground to a grain size of <20 μm.

Test 6

Aluminium oxide C (Degussa) is mixed with lidiuid 1 in the ratio 1:1. The formed saltclike soli is then ground to a grain size of <20 μm.

Test 7

Aluminium hydroxide phosphate (Chemische Fabrik Budenheim) is with with liquid 1 in the ratio 2:1. The formed salt-like solid is then ground to a grain size of <20 μm.

Test group B

Test 8

A homogeneous paste is kneaded from 29 g bis-(acryloxymethyl)-tricyclo[$5.2.1.0^{2.6}$]-decane 15 g 2,2,4-(2,4,4)-trimethylhexamethylene-bis-(urethanethylmethacrylate)

5 g 1,12-dodecandioldimethacrylate 40.4 g silanized Ba-Al-borosilicate glass $d_{50}$=0.7 μm 5 g calcium fluoride 4.5 g silanized Aerosil OX 50 (Degussa)

0.9 g N,N-dimethylaminoethylmethacrylate 0.1 g camphor quinone 0.1 g titanium dioxide and iron pigments.

Test group C

Test 9

In the formulation from test 8, 5 g of the cement powder from test 1 are used instead of the calcium fluoride.

Test 10

In the formulation from test 8, an additional 2 g silanized Ba-Al-borosilicate glass $d_{50}$=0.7 μm and 3 g of the cement powder from test 1 are used instead of the calcium fluoride.

Test 11

In the formulation from test 8, 8 g cement powder from test 1 are used instead of the calcium fluoride and only 37.4 g Ba-Al-borosilicate glass $d_{50}$=0.7 μm.

Test 12

In the formulation from test 8, 5 g of the cement powder from test 2 are used instead of the calcium fluoride.

Test 13

In the formulation from test 8, 5 g of the cement powder from test 3 are used instead of the calcium fluoride.

Test 14

In the formulation from test 8, 5 g of the cement powder from test 4 are used instead of the calcium fluoride.

Test 15

In the formulation from test 8, 5 g of the cement powder from test 5 are used instead of the calcium fluoride.

Test 16

In the formulation from test 8, an additional 2 g silanized Ba-Al-borosilicate glass $d_{50}$=0.7 um and 3 g of the salt from test 6 are used instead of the calcium fluoride.

Test 17

In the formulation from test 8, 5 g of the salt from test 7 are used instead of the calcium fluoride.

Carrying out the Plaque Test

The extent of the plaque accumulation was demonstrated in vitro by the test method described below.

1. Production of small composite plates having a diameter of 10 mm and a height of 1.5 mm.

2. Standardized mechanical polishing of the small plates from 1., with finally 1 μm diamond suspension.

3. Cultivation of the test germs: Streptococcus sanguis, biotype 1, DSM 20068 and Streptococcus mutans, ATCC 25175, DSM 20523 (DSM=German Microorganisms Collection) are in each case cultivated in a bottle with Caso bouillon, the inoculated bouillon being incubated at 30–35° C. until there is marked clouding. To cultivate the test germs, plates from this bouillon comprising Caso bouillon +0.5% agar are in each case inoculated with 0.5 ml and incubated for 2–3 days at 30–35° C.

4. Preparation of the germ suspension: With the help of an inoculation loop the germs from covered plates are suspended in Ringer's solution until there is marked clouding. The germ suspension is then treated for 10 minutes in the ultrasound bath and diluted 1:10 with synthetic saliva solution (Shellis R. P; Archives of Oral Biology; 23, (1978), pp. 485–489 modified according to Glenister D. A., Salamon K. E., et al., Microbial Ecology in Health and Disease; 1, (1988), pp. 31–38) and homogenized. The finished germ suspension contains Streptococcus mutans (ca. $10^7$–$10^8$ CFU/ml) and Streptococcus sanguis (ca. $10^6$–$10^7$ CFU/ml).

5. Test mixture: The small test plates are disinfected in 70% ethanol. In the case of every test mixture, small reference plates of Visio Gem facing composite (Espe) are used for comparison. After the drying, all the small plates which belong to the same sample are transferred together with the help of sterile tweezers into a sterile 100-ml bottle and reacted with 10 ml of the germ suspension, the suspension having to be well homogenized by shaking prior to removal every time. A germ-count check of the germ suspension then takes place. The samples are then incubated for 24 hours at 37° C. and 100 rpm in the shaking-water bath. A further sample of the germ suspension is, together with the small test plates, likewise incubated for 24 hours and its germ count is then checked anew. Following the incubation the small test plates, after decanting of the germ suspension, are transferred into a beaker with 100 ml of Ringer's solution. All the small test plates belonging to one sample are placed in the same beaker. The beaker is then shaken and the small test plates are transferred into a second beaker with the help of sterile tweezers. This procedure is then repeated three times. The small plates are transferred individually from the fifth beaker into test tubes with Ringer's solution with the addition of 1% Tween 20. These small tubes are then treated for 10 minutes in the ultrasound bath. The samples are then thoroughly mixed and a germ count determination is carried out by means of the cast plate method. Caso bouillon with 0.5% yeast extract and 1.5% agar is used as nutrient medium. After cooling, the plates are incubated for 5 days at 30–35° C. Grown colonies are then counted and projected to the total quantity of solution with which the small plates were treated in the ultrasound bath (=CFU/small test plate). At least three tests, each with at least three small buffer plates, are carried out per test series.

6. Calculation: Only tests in which the relative standard deviation within a measurement series is <20% are evaluated. The average is then formed from the three test series.

In addition to the described embodiments, the composite materials Artglass (Kulzer) and Solidex (Shofu) customary in the trade were also included in the study.

Test results

The following table gives an overview of the test results in percentages relative to the small reference plates of Visio Gem:

| Material | Streptococcus mutans | Streptococcus sanguis |
|---|---|---|
| State of the art | | |
| Artglass | 91.5 ± 4 | 96.7 ± 4.4 |
| Solidex | 107.7 ± 4.8 | 92.6 ± 5.4 |
| Test 8 | 97.7 ± 6.4 | 73.5 ± 7.4 |
| Invention | | |
| Test 9 | 57.8 ± 7.3 | 28.9 ± 11.8 |
| Test 10 | 64.8 ± 8.1 | 44.1 ± 14.2 |
| Test 11 | 37.2 ± 6.0 | 19.3 ± 3.6 |
| Test 12 | 63 ± 8.1 | 33.0 ± 6.3 |
| Test 13 | 22.9 ± 8.5 | 20.7 ± 7.4 |
| Test 14 | 86.6 ± 17.1 | 67.0 ± 5.1 |
| Test 15 | 64.9 ± 15.9 | 42.9 ± 13.1 |
| Test 16 | 73.5 ± 7.4 | 40.2 ± 5.3 |
| Test 17 | 39.6 ± 4.6 | 43.3 ± 4.5 |

EXAMPLE 2

The effect according to the invention of reducing the accumulation of plaque was also demonstrated in viva using the following test method: the total prosthesis of a subject was ground back at the false teeth "11" and "12". One tooth was faced with a plastic facing material customary in the trade (Visio Gem, Espe), the other with the composite material according to the invention from test 9. After six weeks' wear without special hygiene instructions the prosthesis was examined. The plaque which had accumulated during the wearing period was clearly coloured red with "plaque check DS 2" colouring solution (Hu-Friedy), as a result of which a digital recording and evaluation was made possible. The effect according to the invention is easily recognizable in the illustration of FIG. 1. The illustration shows the subject's total prosthesis, in which one tooth (numbered 1) was faced with composite material according to the invention from test 9, and the tooth numbered 2 was treated with the material customary in the trade (Visio Gem, Espe). The dark sites shown in this black-and-white picture correspond to the plaque accumulations coloured red by the mentioned plaque-colouring solution. A digital evaluation gave a difference of cat 67% in plaque accumulation between tooth 1 and tooth 2.

EXAMPLE 3

The effect according to the invention of reducing plaque accumulation was also demonstrated via the zeta potential according to C. Werner, H.-J. Jacobasch, G. Reichelt, J. Biomat. Sci. Polymet. Edn., 7 (1995), No. 1, 61–76. In this respect, N. Satou et al. published in the Journal of Material Science (1996), 749–752 the theory that the accumulation of bacteria can be prevented by negative surface potentials. According to this theory a direct relationship exists between the zeta potential and the number of Streptococcus mutans, Streptococcus sanguis and Streptococcus sobrinus colonies on a surface.

Two testpieces each measuring 20×10×1.5 mm with a surface polished to 1 μm are subjected to the measurement procedure; as well as the described embodiments, the composite material Visio Gem (Espe) customary in the trade was included in the study. The following results were obtained:

| Material | ζ [mV] at pH = 7 |
|---|---|
| Visio Gem | −40 |
| Test 8 of Example 1 | −44 |
| Test 9 of Example 1 | −77 |
| Test 9 of Example 1 | −77 |
| Test 10 of Example 1 | −60 |
| Test 11 of Example 1 | −80 |

It is clear that, with an increasing polysalt content in otherwise comparable compositions, the zeta potential becomes more negative.

EXAMPLE 4

To show that the effect according to the invention, unlike plaque-inhibiting materials from the state of the art, occurs without a significant release of fluoride ions, the release of fluoride ions was measured in the case of the materials of test group C, which contain ground glass ionomer cements from fluoride-containing glasses. To this end, two testpieces 15 mm in diameter and 1.5 mm high were stored freely suspended in 50 ml of distilled water at 36° C. and the concentration of fluoride ions was measured, after the respective storage periods of 1 day and 7 days, by means of an ion-sensitive electrode. The water was changed after every measurement. The detection limit of the method used is 0.1 ppm fluoride.

| Material from test no. of Example 1 | 9 | 10 | 11 | 12 | 13 | 14 | 15 |
|---|---|---|---|---|---|---|---|
| Fluoride concentration after 1d [ppm] | <0.1 | <0.1 | 0.2 | <0.1 | <0.1 | <0.1 | 0.1 |
| Fluoride concentration after 7d [ppm] | 0.1 | <0.1 | 0.1 | <0.1 | 0.1 | 0.2 | 0.2 |

We claim:

1. A dental composite composition, comprising:
    (a) one or more ethylenically unsaturated, polymerizable monomers on the basis of mono-, di- or polyfunctional (meth)acrylates;
    (b) an initiator;
    (c) a filler; and
    (d) one or more salts of acid-functional polymers having mono- or polyvalent cations.

2. The dental composite composition according to claim 1, wherein component (d) is a sodium, calcium, aluminum, zinc, yttrium or lanthanum salt of a polymeric carboxylic acid, selected from the group consisting of polymaleic acid, polyacrylic acid, polyitaconic acid, maleic acid/acrylic acid copolymers, acrylic acid/itaconic acid copolymers, a polymeric phosphonic acid, and mixtures thereof.

3. The dental composite composition according to claim 1, wherein component (d) is a cured glass ionomer cement based on calcium or strontium aluminum fluorosilicate glasses.

4. The dental composite composition according to claim 1, wherein component (d) has been ground to a small grain size of below 20 μm.

5. The dental composite composition according to claim 1, wherein component (d) is present in a quantity of 1 to 20 wt. %, relative to the total weight of the composition.

6. A dental composite composition in the form of a material for prostheses, temporary fixtures, facing, fillings, a plastic for an orthodontic apparatus, false teeth, stump construction or a dental cement, wherein said composition comprises:
    (a) one or more ethylenically unsaturated, polymerizable monomers on the basis of mono-, di- or polyfunctional (meth)acrylates;
    (b) initiator;
    (c) a filler; and
    (d) one or more salts of acid-functional polymers having mono- or polyvalent cations.

7. A method of providing plaque-inhibiting properties to a dental composite composition, said method comprising the step of:
    adding salts of acid-functional polymers having mono- or polyvalent cations, in a plaque-inhibiting amount to said dental composite composition.

8. The method of claim 7, wherein said dental composite composition is a cured glass ionomer cement.

9. The dental composite composition according to claim 1, wherein components (a) to (d) are present in the following ranges:
    (a) 4 to 68.99 wt.-%;
    (b) 0.01 to 3 wt.-%;
    (c) 5 to 95 wt.-%; and
    (d) 1 to 20 wt.-%.

10. The dental composite composition according to claim 1, wherein components (a) to (d) are present in the following ranges:
    (a) 45 to 55 wt.-%;
    (b) 0.1 to 2 wt.-%;
    (c) 20 to 80 wt.-%; and
    (d) 2 to 15 wt.-%.

11. The dental composite composition according to claim 10, wherein component (d) is present in an amount of 3 to 9 wt.-%.

12. The dental composite composition according to claim 1, wherein component (d) is a cured glass ionomer cement, which contains:
    (1) an aluminum fluorosilicate glass or an aluminum silicate glass; and
    (2) a sodium, calcium, aluminum, zinc, yttrium or lanthanum salt of a polymeric carboxylic acid, selected from the group consisting of polymaleic acid, polyacrylic acid, polyitaconic acid, maleic acid/acrylic acid copolymers, acrylic acid/itaconic acid copolymers, a polymeric phosphonic acid, and mixtures thereof.

13. The dental composite composition according to claim 12, wherein component (d) comprises particles having an average grain size of at least 3 μm.

14. The dental composite composition according to claim 12, wherein component (d) comprises particles having a maximum grain size of 20 μm.

15. The dental composite composition according to claim 12, wherein component (a) is an ethylenically unsaturated monomer or polymer of an acrylate or methacrylate; component (b) is selected from the group consisting of benzoin alkyl ether, benzil cetals, acylphosphine oxides, aliphatic 1,2-diketone compounds, and aromatic 1,2-diketone compounds; and component (c) is an inorganic filler selected from the group consisting of quartz, ground glasses, silica gels, and pyrogenic silicic acids.

16. The dental composite composition according to claim 12, further comprising as component (e) a member selected from the group consisting of pigments, X-ray-opaque additives, thixotrophic auxiliaries and plasticizers.

17. The dental composite composition according to claim 1, further comprising as component (e) a member selected from the group consisting of pigments, X-ray-opaque additives, thixotrophic auxiliaries and plasticizers.

* * * * *